United States Patent [19]

Knowles et al.

[11] Patent Number: 4,727,036

[45] Date of Patent: Feb. 23, 1988

[54] ANTIBODIES FOR USE IN DETERMINING HEMOGLOBIN $A_{1c}$

[75] Inventors: William J. Knowles, Hamden; Vincent T. Marchesi, Guilford; Wallace Haigh, North Haven, all of Conn.

[73] Assignee: Molecular Diagnostics, Inc., West Haven, Conn.

[21] Appl. No.: 779,731

[22] Filed: Sep. 27, 1985

Related U.S. Application Data

[63] Continuation-in-part of Ser. No. 763,193, Aug. 8, 1985, Pat. No. 4,647,654, which is a continuation-in-part of Ser. No. 665,811, Oct. 29, 1984, abandoned.

[51] Int. Cl.$^4$ .............. G01N 33/72; G01N 33/577; C12P 21/00; C12N 5/00
[52] U.S. Cl. .................................. 436/547; 424/85; 530/387; 435/240.27
[58] Field of Search .............. 436/547; 435/68, 172.2, 435/240, 241; 424/85, 101; 530/387

[56] References Cited

U.S. PATENT DOCUMENTS

| | | | |
|---|---|---|---|
| 4,247,533 | 1/1981 | Cerami et al. | 436/542 |
| 4,423,034 | 12/1983 | Nakagawa et al. | |
| 4,478,744 | 10/1984 | Mezei et al. | 424/85 |

FOREIGN PATENT DOCUMENTS

| | | |
|---|---|---|
| 0111211 | 6/1984 | European Pat. Off. |
| 201187 | 11/1986 | European Pat. Off. |
| 3439610 | 4/1986 | Fed. Rep. of Germany |
| 1580318 | 12/1980 | United Kingdom |

OTHER PUBLICATIONS

Scientific American, (1980), pp. 66–74, Milstein.
Dixon, *Biochem. J.*, (1972), 129, 203–208.
Clinical Chemistry, vol. 30, No. 11, Nov. 1984, pp. 1746–1752.

*Primary Examiner*—Delbert R. Phillips
*Assistant Examiner*—Nathan M. Nutter
*Attorney, Agent, or Firm*—Sprung Horn Kramer & Woods

[57] ABSTRACT

Monoclonal antibodies specific for the glucosylated N-terminal peptide residue in Hb $A_{1c}$, a method for producing such antibodies, hybridoma cell lines secreting such antibodies and a method for their production, and immunoassay methods and reagent systems using such antibodies for the determination of Hb $A_{1c}$ in human blood samples. The monoclonal antibodies are secreted by hybridomas obtained from the fusion of a myeloma cell and a lymphocyte which has been taken from an animal, preferably a mouse, immunized with a synthetic peptide immunogen and which produces antibody specific for the glucosylated N-terminal peptide residue in Hb $A_{1c}$. The synthetic peptide immunogen comprises an N-terminal plucosylated peptide residue having at least 2 amino acid units corresponding to the N-terminus of the beta-subunit of human hemoglobin and an immunogenic carrier to which the glucosylated peptide residue is linked. The immunoassay involves treatment of the blood sample to expose the glucosylated N-terminal peptide epitope and detection thereof by binding of the specific monoclonal antibody or a fragment thereof.

20 Claims, 8 Drawing Figures

ANTIBODIES FOR USE IN DETERMINING HEMOGLOBIN A$_{1c}$

CROSS-REFERENCE TO RELATED APPLICATION

This application is a continuation-in-part application of application Serial No. 763,193, filed Aug. 8, 1985, now U.S. Pat. No. 4,647,654, which is a continuation-in-part application of application Ser. No. 665,811, filed Oct. 29, 1984, and now abandoned.

BACKGROUND OF THE INVENTION

This invention relates to the determination of the glucosylated form of hemoglobin known as Hb A$_{lc}$ in human blood samples. The determination of the extent of glucosylation of hemoglobin in an individual's blood provides a useful index of glucose level control in diabetics. In particular, the present invention concerns the preparation of monoclonal antibodies which recognize specifically the glucosylated N-terminal peptide residue in such human hemoglobin.

Patients afflicted with diabetes are incapable of metabolizing glucose in a conventional manner resulting in a build-up of glucose in their blood and urine. Conventionally, the glucose level in such body fluids is taken as a measure of the state of the diabetic condition which, in turn, is used as a guide for the amount of insulin or other agent to be taken or of the need to change the patient's diet.

This works moderately well except that the glucose level may fluctuate widely in dependence upon the time and content of the last meal, the last insulin injection, and the like. Thus, the reading will reflect an instantaneous condition which might not truly identify the longer term state of the diabetic condition. To circumvent the single glucose determination, more elaborate measurements (e.g., the 4 to 8 hour glucose tolerance tests) are used to measure the blood levels of glucose following an oral administration. These latter tests are time consuming, expensive and the individual must fast during the course of the assay.

It is known that another effect of the diabetic condition is an increase in the amount of glucosylated hemoglobin (Hb) in the blood of the diabetic. Hemoglobin is a protein tetramer made up of four chains (subunits) of amino acids, each of about 143 units and having a total molecular weight of about 64,000. At one end of the molecule (the NH$_2$-terminus of the beta-subunit) there is a valine unit which can react with glucose. The glucosylation of hemoglobin occurs by a non-enzymatic reaction involving glucose and the alpha-amino group of valine. Following a Schiff base formation between the reactants, the glucose undergoes an Amadori rearrangement forming 1-deoxyfructovaline. This complex is covalent and is not reversible. The glucosylation reaction is governed by the concentration of the reactants, e.g., hemoglobin and glucose. In a normal (non-diabetic) individual approximately 3% of the total hemoglobin is glucosylated. Hemoglobin tetramers with a 1-deoxyfructo-valine on the N-terminus of a beta-chain are identified as being glucosylated or A$_{1c}$ hemoglobin.

Glucose levels in diabetics are sufficiently high to increase the rate of glucosylation in direct dependence upon the glucose level in the blood, which reflects the severity of the diabetic condition. With hemoglobin, the A$_{1c}$ level is raised to about 5 to 12%. Since the circulating life span of hemoglobin is about 120 days, a glucosylated hemoglobin measurement will give a value which reflects an average glucose level for that period. Notably a meal high in glucose will not be reflected in a high glucosylated hemoglobin or serum albumin level. Thus, measurement of the glucosylated hemoglobin content gives a truer picture of the average circulating glucose levels and thus a truer picture of the long term condition of the patient.

One way of using this measurement has involved passing a lysed blood sample through a boronate column, thereby selectively adsorbing the A$_{lc}$ fraction of the hemoglobin along with some other undesired glucosylated non-specific components. The column is washed and the A$_{lc}$ determined spectrophotometrically. The process is complex, time consuming, and temperature dependent, and sometimes gives variable results.

An alternative analytical method involved subjecting a lysed blood sample to electrophoresis but electrophoresis is slow and expensive and requires considerable operator skill so the test is not practical for a clinical laboratory.

Dixon in Biochem. J.(1972)129,203–208 reacted glucose with valylhistidine but solely for experimental purposes, no utility being expressed for the product.

U.S. Pat. No. 4,247,533 discloses an analytical technique wherein antibodies to Hb A$_{lc}$ were reportedly raised in a special sheep by injection of Hb A$_{lc}$ and absorbed with nonglucosylated hemoglobin to provide polyclonal antibodies which distinguished between Hb A$_{lc}$ and nonglucosylated Hb. Such antibodies then form the basis for a test to determine the proportion of glucosylated hemoglobin in a sample. The test, however, requires an appropriately immunized sheep and antibody absorptions to attain the proper specificity. It is, therefore, costly and difficult to produce specific polyclonal antibodies. The antibody preparations produced by this absorption approach are reported to be of low titer and affinity. The reproducibility of this approach is also open to question since there are no recent reports describing its use for the analysis of clinical samples of human hemoglobin.

Another attempt to obtain antibodies specific for Hb A$_{lc}$ is found in U.S. Pat. No. 4,478,744. The workers in U.S Pat. No. 4,478,744 substituted a synthetic peptide immunogen for the normal hemoglobin molecule as the immunizing agent injected into an animal which normally does not have Hb A$_{lc}$ in its bloodstream, e.g., sheep. The synthetic peptide immunogen comprised a glucosylated peptide residue having an amino acid sequence corresponding to between the first 4 to 10 amino acids in the N-terminal hemoglobin sequence. Subsequent investigations, reported hereinbelow, have found that the sheep polyclonal antiserum raised against the synthetic peptide immunogen has no detectable speificity for the glucosylated form, Hb A$_{lc}$.

| Definitions | |
| --- | --- |
| Amino Acid | Abbreviation |
| Arginine | Arg |
| Aspartic Acid | Asp |
| Glutamic Acid | Glu |
| Lysine | Lys |
| Serine | Ser |
| Asparagine | Asn |
| Glutamine | Gln |
| Glycine | Gly |
| Proline | Pro |
| Threonine | Thr |
| Alanine | Ala |
| Histidine | His |
| Cysteine | Cys |
| Methionine | Met |
| Valine | Val |
| Isolencine | Ile |
| Leucine | Leu |
| Tyrosine | Tyr |
| Phenylalanine | Phe |
| Tryptophan | Trp |
| Alpha-Aminobutyric Acid | Aba |

SUMMARY OF THE INVENTION

It is accordingly an object of the present invention to provide a comparatively simple, inexpensive, reliable test for determining the long-term blood sugar level of a patient based on the immunoassay determination of Hb $A_{Ic}$.

It is another object of the invention to provide such a test for determining the content of glucosylated hemoglobin, Hb $A_{1c}$, in a patient's whole blood sample.

These and other objects and advantages are realized in accordance with the present invention pursuant to which there are provided monoclonal antibodies, or fragments thereof comprising an antibody binding site, which will selectively react with the glucosylated peptide N-terminal residue in Hb $A_{Ic}$, but not with non-glucosylated forms of such protein so that the extent of reaction is a measure of the N-terminal glucosylated content which, in turn, is a measure or index of the diabetic condition.

It is a further object of the invention to provide cell lines which will readily produce such monoclonal antibodies having desired specificity for glucosylated peptide residues, specifically the residue found in Hb $A_{Ic}$.

The present invention now provides the means for a highly specific immunoassay determination of glucosylated hemoglobin in biological fluids such as whole blood. Monoclonal antibodies raised against the synthetic glucosylated N-terminal peptide residues appearing in Hb $A_{Ic}$ have been found to bind specifically to such residues in the glucosylated beta-subunit of hemoglobin. The antibodies can be prepared in a variety of manners following conventional antiserum and monoclonal techniques. Principally, the antibodies are prepared against a synthetically derived immunogen comprising the desired glucosylated N-terminal peptide residue chemically linked to an immunogenic carrier, the glucosylated peptide having at least 2, and preferably from about 5 to 15, amino acid units corresponding to Hb $A_{Ic}$. The resultant monoclonal antibodies are specific for the glucosylated synthetic peptide and the corresponding exposed epitope for the hemoglobin $A_{Ic}$ molecule.

Monoclonal antibodies specific to Hb $A_{Ic}$ found in human blood are secreted by hybridomas derived from fusion of myeloma cells and lymphocytes taken from an animal that had been immunized with a synthetic peptide immunogen. The synthetic peptide immunogen will preferably be of the formula:

wherein Glyco-(NH)Val represents a nonenzymatically glucosylated valine residue, His represents the second amino acid in the native beta-subunit Hb sequence, AA is a bond or one or more amino acid residues, R is an appropriate linking group, Carrier is an immunogenic carrier material, and n is on the average from 1 to the number of available coupling sites on the Carrier. Linking group R can consist of any desired coupling reagent and AA can comprise one or more additional amino acid residues corresponding to the carbohydrate-bearing N-terminus of the beta-subunit of human hemoglobin. For example, -AA- can be selected from the following amino acid sequence or any continuous fragment thereof which begins with the leucine unit: -Leu-Thr-Pro-Glu-Glu-Lys-. In addition, linking group R can consist of additional amino acid units not found in normal human hemoglobin but which can be conveniently added by peptide synthesis methods and can serve as useful functional groups for coupling to the carrier material. A particularly useful linking group is -Tyr-Tyr-Cys which provides a unique thiol group for controllably coupling the glucosylated peptide unit to carrier materials.

The present invention particularly provides a monoclonal antibody, preferably raised in mice, specific to the carbohydrate-bearing N-terminus of the beta-subunit of human hemoglobin. The antibody is characterized by the ability to bind a nonenzymatically glucosylated peptide having at least 2, and particularly from about 5 to 15, amino acid units corresponding to the glucosylated N-terminal sequence of the beta-subunit of hemoglobin, as well as the ability to bind to such N-terminal sequence on hemoglobin itself.

Figure 1:
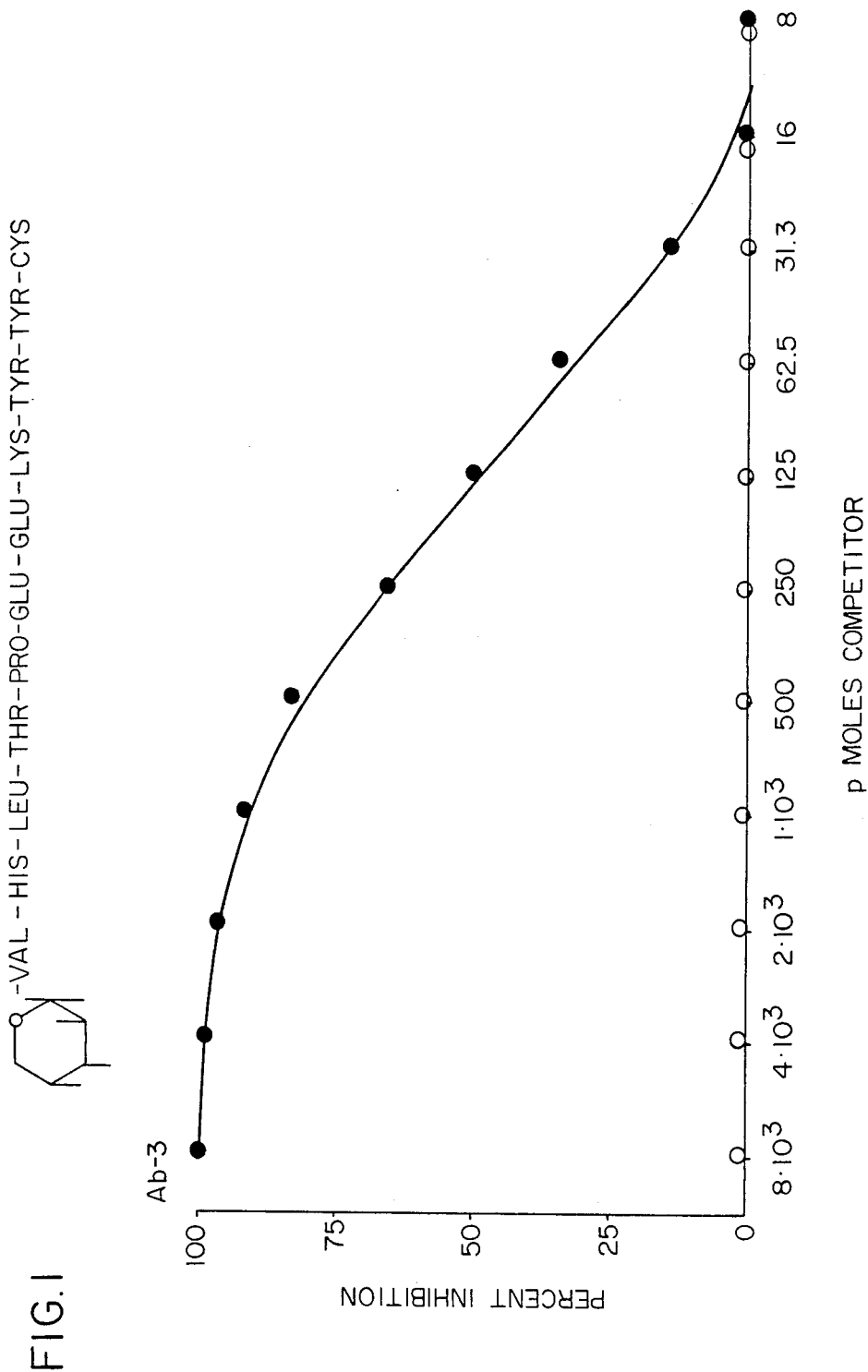
FIG. 1 is a plot depicting the inhibition of Ab-3 binding to $A_{Ic}$ by glycopeptide 1 (PEPTIDE 1). Antibody was preincubated with glycopeptide before transfer into an $A_{Ic}$ coated microtiter plate. The monoclonal antibody that binds to $A_{Ic}$ was detected using a secondary antibody - enzyme. The results are plotted in FIG. 1 as a percent inhibition where 0% inhibition is the value obtained with no competitor. The 0 - 0 line is from an identical peptide that lacks the carbohydrate, indicating the carbohydrate is essential for antibody binding. All points are the mean of triplicate measurements.

The competition experiment was conducted as described for FIG. 1.

Figure 4:
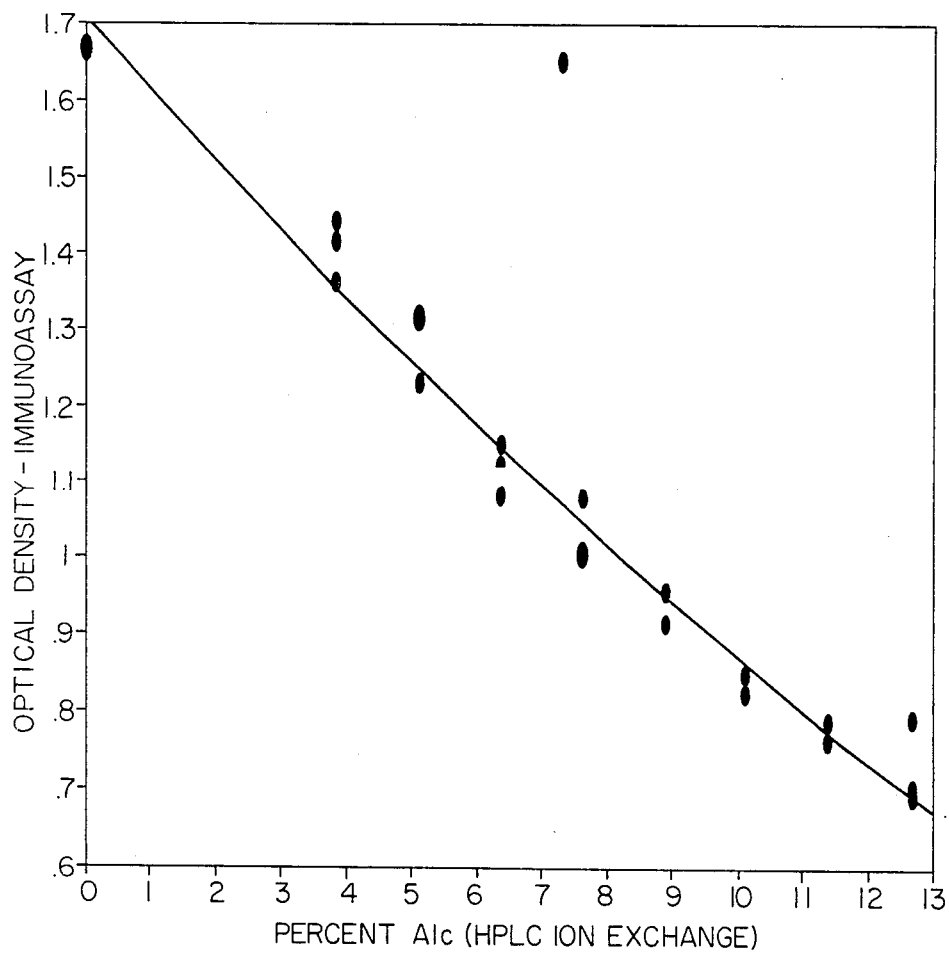

FIG. 4 is a typical standard curve using optimal assay conditions. The whole blood standard was prepared using different ratios of denatured whole blood from a diabetic having 12.66% $A_{lc}$ as measured by HPLC ion exchange with whole blood from a normal donor (3.83% $A_{lc}$). All points of triplicate measurements are plotted.

Figure 5:
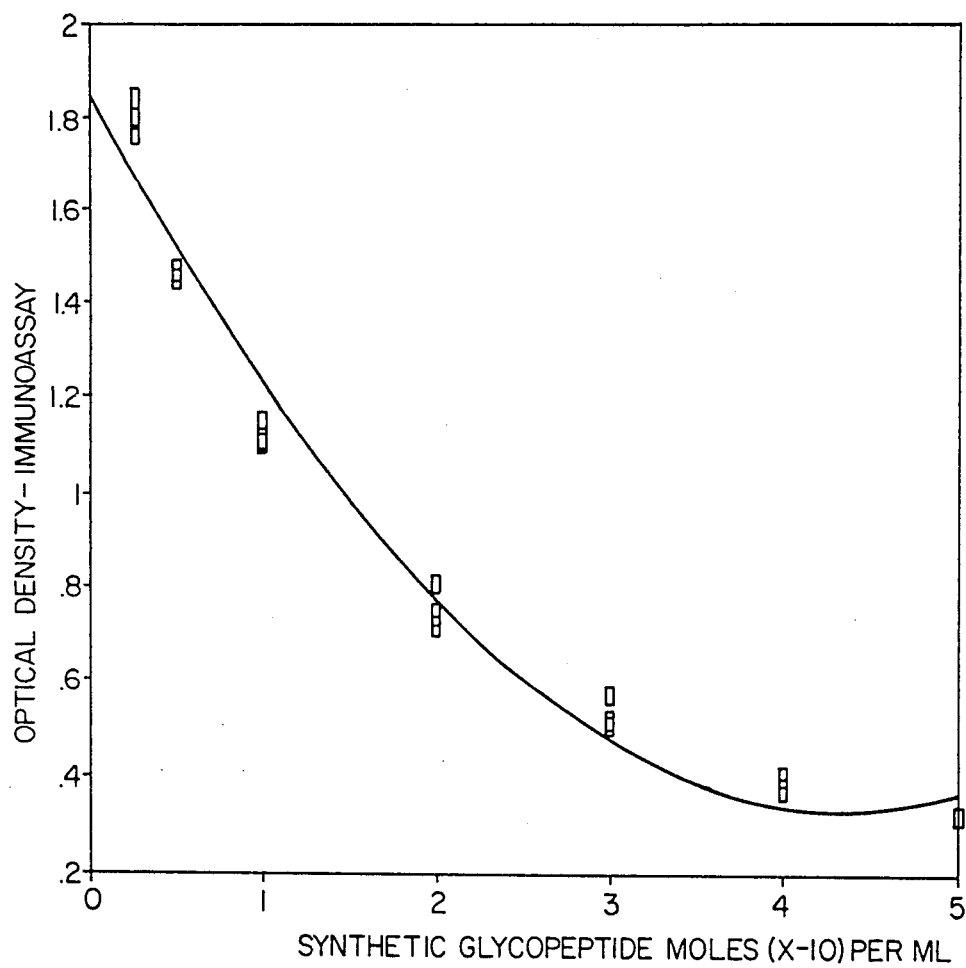

FIG. 5 is a standard curve using a synthetic peptide standard. The assay was performed as described for FIG. 4, except that instead of using whole blood, different amounts of synthetic glycopeptide were used as the competitor. All values of triplicate determinations were plotted.

Figure 6:
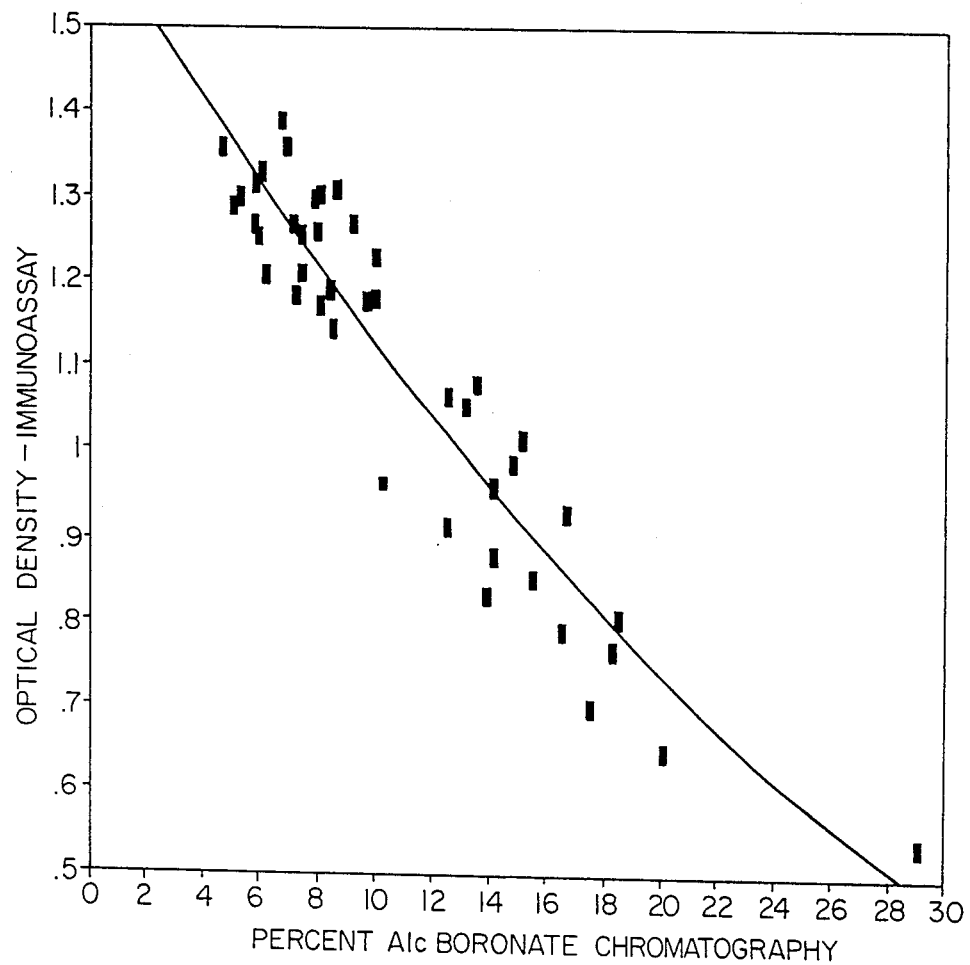

FIG. 6 is a plot depicting a comparison of the immunoassay method with the boronate affinity method for donors. The mean of triplicate determinations are plotted for the immunoassay coordinate.

Figure 7:
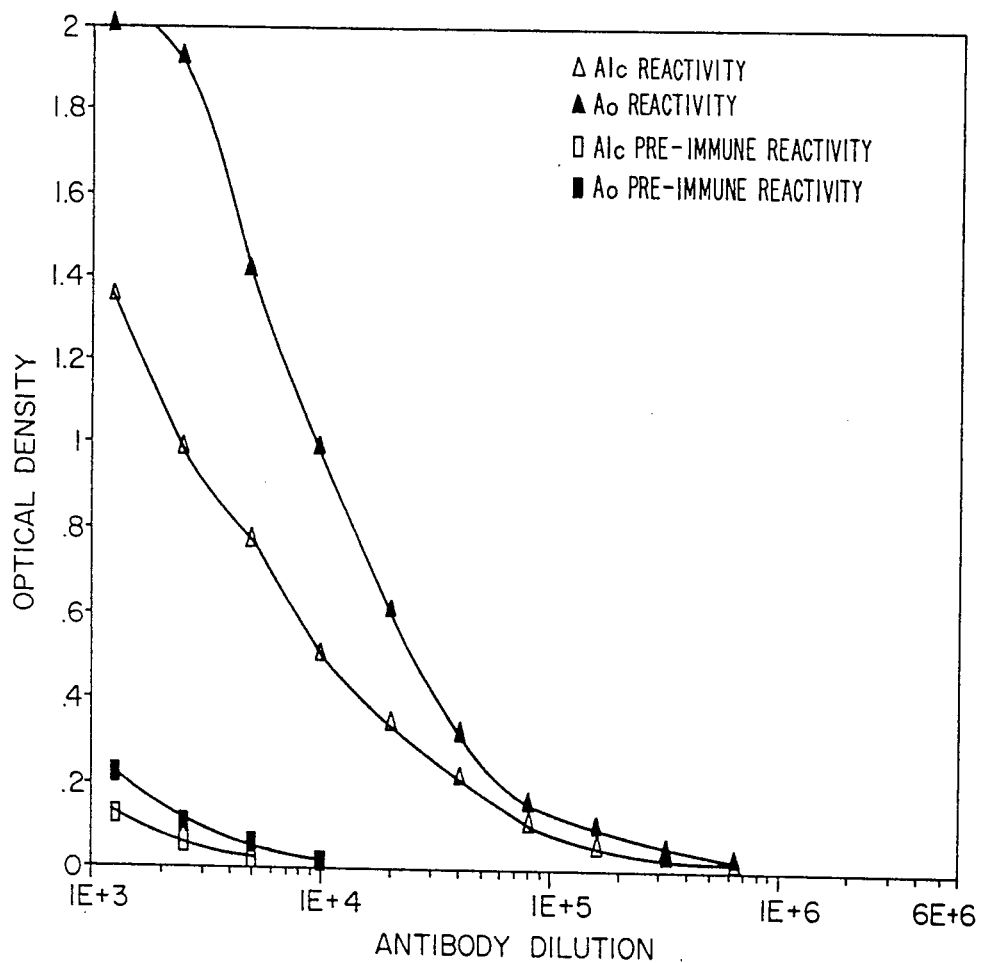

FIG. 7 is a plot depicting the results of immunizing a sheep with the synthetic glycopeptide of Example 1(b).

Figure 8:
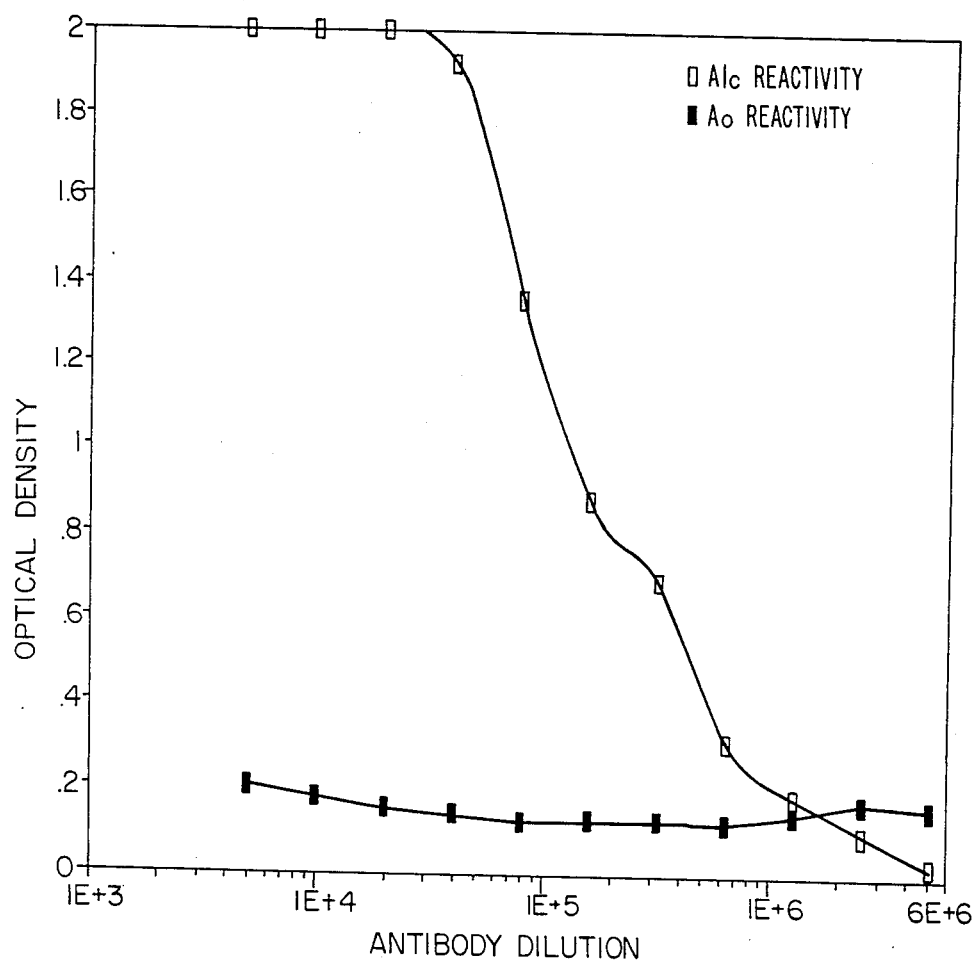

FIG. 8 is a plot demonstrating that mouse monoclonal antibodies are specific for $A_{lc}$ hemoglobin.

DETAILED DESCRIPTION OF THE INVENTION

The monoclonal antibody of the present invention is principally characterized by its specificity for binding the glucosylated form of the N-terminal peptide sequence of the beta-subunit of human hemoglobin. This glucosylated residue is the distinguishing structural feature of Hb Alc. An antibody of the present invention requires an epitope or determinant site comprising minimally the 1-deoxyfructosyl carbohydrate unit, formed upon Amadori rearrangement of the reaction product between glucose and the terminal amine, and a peptide sequence extending therefrom comprising at least one of the amino acid units of the Hb $A_{lc}$ N-terminal sequence in the position corresponding to the native Hb $A_{lc}$ sequence. The other amino acid units in the peptide sequence characterizing the epitope may be the same or different as those appearing in the native Hb $A_{lc}$ sequence. In this way, the epitope is characterized by at least two contact or binding sites with the antibody which sites are unique to the glucosylated N-terminal Hb $A_{lc}$ sequence. Preferably the antibody will specifically bind a glucosylated peptide residue of the formula:

Glyco-(NH)Val-His-AAwherein Glyco-(NH)Val and AA are as defined above. Particularly preferred monoclonal antibodies have been found to be specific for the glucosylated dipeptide residue irrespective of the nature of AA. Antibodies with specificity requiring glucosylated peptide sequences of greater length are also obtainable with AA being a sequence of from 1 to 12, preferably 1 to 6, amino acids corresponding to the N-terminus of the beta-subunit of human hemoglobin. Such specificity of the monoclonal antibody enables the specific detection of the exposed glucosylated N-terminal peptide residue in Hb $A_{lc}$ to the substantial exclusion of other glucosylated peptide epitopes on hemoglobin and other proteins and peptides native to the human bloodstream.

The glucosylated N-terminal peptide residue on the native Hb $A_{lc}$ molecule is made accessible to the monoclonal antibody or a fragment thereof of the present invention by appropriate denaturation or digestion of the protein in the sample to be assayed. An underlying hypothesis for the success of the present invention in obtaining specific antibodies where prior art attempts have failed will now be discussed, but its correctness should not be interpreted as being critical to the inventiveness of the present method.

The N-terminal sequence of the beta-subunit of human hemoglobin is quite similar to the corresponding sequence of mouse hemoglobin, the first four amino acids being identical. Secondly, mouse hemoglobin is glucosylated to approximately the same extent as human hemoglobin. Thus, in the native human hemoglobin molecule the N-terminal sequence of the beta-subunit would not be seen by the mouse as foreign and an immune response would not be expected. This is the logic of the prior art workers who accordingly chose an animal (sheep) that has a quite different hemoglobin protein sequence, and is not glucosylated in the hopes of obtaining an immune response. However, the present invention has revealed that when the glucosylated N-terminal residue is exposed to the mouse immune system in the form of a synthetic peptide immunogen, the epitope is presented in a configuration to which the mouse can respond immunologically. Through somatic cell cloning techniques, hybridomas secreting highly specific antibodies can be isolated. The secreted antibodies will bind to the glucosylated N-terminal peptide residue in the native hemoglobin molecule if it has been exposed sufficiently for interaction with the combining site on the antibody. The manner of exposure of the epitope is discussed in more detail below.

Specifically, hybridoma cell lines are raised to produce antibodies only against the glucosylated portion of the hemoglobin molecule rather than to the entire protein and such cell lines and their antibodies are screened to identify and isolate those monoclonal antibodies which will thereafter react selectively with the glucosylated Hb $A_{lc}$ epitope.

To produce such antibodies, a fragment of the protein chain, corresponding to the naturally occurring glucosylated peptide sequence, is coupled to a protein carrier and injected into a laboratory animal to elicit an immune response. Lymphocytes such as spleen cells from the immunized animal are fused with myeloma cells to produce hybridomas which are cultured and screened for production of monoclonal antibodies. The monoclonal antibodies are screened for those selective to the glucosylated peptide epitope and the particular cell line is cloned for use in producing further quantities of the monoclonal antibody.

To produce antibodies in the laboratory animal, e.g., BALB/c mice, rats or the like, a glucosylated hemoglobin fragment must be either produced and isolated from naturally occurring human hemoglobin or be chemically synthesized and purified. The hemoglobin fragment should include the 1-deoxyfructose residue and at least 2 amino acid units, preferably 3,4,5 or even more, corresponding to the N-terminus of the beta-subunit of hemoglobin (valinehistidine). Advantageously it includes about 5 to 15 and preferably about 7 to 10 units.

To ensure that the glucosylated peptide fragment is optimally antigenic it can be advantageously coupled to a carrier material comprising a large immunogenic molecule such as bovine serum albumin (BSA) or keyhole limpet hemocyanin (KLH). The fragment should also carry the natural rearranged adduct of the glucose-valine reaction which can be present from the outset, as in the case of the isolated naturally occurring hemoglobin fragment, or, preferably, can be formed on the synthetic peptide during its synthesis or before coupling the peptide to the large protein carrier. The carrier can be added in any manner which does not destroy the antigenicity of the fragment.

The glucosylated fragment can be produced by chemical or enzymatic digestion of naturally occurring Hb, e.g., $A_{lc}$. This fragment can be coupled to a carrier using classical coupling procedures, e.g., glutaraldehyde or carbodiimide, and the conjugate used as an immunogen.

A preferred manner of chemically synthesizing a portion of the known hemoglobin sequence involves the addition of one or more amino acid units (not found in the normal sequence) for optimizing its antigenicity and coupling properties. In this case, the final unit carries a thiol (SH) group by which it can be coupled to the ligand in a conventional manner, as by reaction with a bifunctional linking reagent such as m-maleimidobenzoyl N-sulfosuccinimide ester (MBS).

In accordance with a preferred embodiment, to the lysine end of a synthetic Hb fragment carrying the eight units $NH_2$-valine-histidine-leucine-threonine-proline-glutamic acid-glutamic acid-lysine-COOH there were added tyrosine, tyrosine and cysteine, resulting in an 11-unit cysteine-terminated peptide.

This can be glucosylated in conventional manner by nonenzymatic reaction with glucose. The glucopeptide thereafter is coupled to a large carrier to produce the antigen which is administered to produce the antibodies. Lymphocytes from the animal which produce antibody to the glucosated peptide epitope are then fused in conventional manner to produce hybridomas which are cloned and those producing monoclonal antibodies of the desired specification are further subcloned. The cell line(s) whose monoclonal antibodies show the greatest selectivity for the glucosylated epitope, as opposed to non-glucosylated Hb, are then propagated and the antibodies harvested. Reviews of such monoclonal antibody techniques are found in Lymphocyte Hybridomas, ed. Melchers et al, Springer-Verlag (New York 1978), Nature 266:495 (1977), Science 208:692 (1980), and Methods in Enzymology 73(Part B):3–46 (1981).

The antibodies can then be used in conventional manner to react with blood samples containing unknown quantities of glucosylated Hb and the extent of reaction can be compared with calibrated standards to determine the extent of glucosylation. The read-out can be by fluorescence, by immunoassay, or the like, by joining suitably readable groups to the monoclonal antibodies in known manner without loss of their binding power for the glucosylated epitope in Hb $A_{lc}$.

Alternatively, an assay based on a reagent test strip can be run in which a carboxyl-carrying material such as carboxylmethyl-cellulose is coated onto a strip of wood or plastic. Then the strip is dipped into the lysed and denatured unknown blood sample, thereby adsorbing the hemoglobin, glucosylated or not. The strip is then dipped into a solution of the monoclonal antibodies, suitably labeled (e.g., enzyme, fluorescence, cofactors, etc.) at a site which does not interfere with binding to the Hb $A_{lc}$ epitope. The amount of antibody bound is determined by the amount of label on the strip and is an indication of the amount of glucosylated Hb in the unknown sample. The attachment of the label and its readout are effected in conventional manner.

The immunogen used to stimulate production of appropriate immunoglobulins in the most general sense will comprise one or more of the glucosylated peptide residues chemically linked to an immunogenic carrier material. The immunogenic carrier material can be selected from any of those conventionally known having functional groups available for coupling to the glucosylated peptide residue. In most cases, the carrier will be a protein or polypeptide, although other materials such as carbohydrates, polysaccharides, lipopolysaccharides, nucleic acids, and the like of sufficient size and immunogenicity can likewise be used. For the most part, immunogenic proteins and polypeptides will have molecular weights between 4,000 and 10,000,000, preferably greater than 15,000, and more usually greater than 50,000. Generally, proteins taken from one animal species will be immunogenic when introduced into the blood stream of another species. Particularly useful proteins are albumins, globulins, enzymes, hemocyanins, glutelins, proteins, having significant nonproteinaceous constituents, and the like. Further reference for the state-of-the-art concerning conventional immunogenic carrier materials and techniques for coupling haptens thereto may be had to the following: Parker, Radioimmunoassay of Biologically Active Compounds, Prentice-Hall (Englewood Cliffs, N.J. USA, 1976); Butler, J. Immunol. Meth. 7:1–24(1974); Weinryb and Shroff, Drug Metab. Rev. 10:271–283(1974); Broughton and Strong, Clin. Chem. 22:726–732(1976); and Playfair et al, Br. Med. Bull. 30:24–31(1974).

The letter "n" in the above formulas represents the number of glucosylated residues that are conjugated to the carrier, i.e., the epitopic density of the immunogen, and will range from 1 to the number of available coupling sites on the carrier and can be as high as 5000 in the case of certain high molecular weight synthetic polypeptides such as polylysine The epitopic density on a particular carrier will depend upon the molecular weight of the carrier and the density of available coupling sites. Optimal epitopic densities, considering the ease and reproducibility of synthesis of the immunogen and antibody response, fall between about 10% and about 50% of the available coupling groups on the carrier involved.

Linking group R can be essentially any convenient and stable structure. Such linking group R will usually be in the form of an aliphatic chain comprising between 1 and about 20 atoms, excluding hydrogen, and including heteroatoms such as nitrogen, oxygen, and sulfur. The glucosylated residue can be joined through a variety of groups to form linking chain R, including methylene, ether, thioether, imino, and the like. One skilled in the art will have a wide variety of linking groups from which to choose to prepare the immunogen. Normally, the glucosylated peptide will be prepared terminating in a functional group such as amino, carboxyl, thiol, hydroxyl, or maleimido which is active in a coupling reaction to an appropriate group in the carrier molecule.

The antibody selected for use in an immunoassay can be of any immunoglobulin class, e.g., IgG, IgM, and so forth, and of any subclass thereof. Normally, the antibody will be of the IgG class and if desirable any fragment of such antibody can be used which contains an antibody combining site, e.g., Fab, F(ab'), and F(ab')$_2$. The selected antibody reagent can be used in any immunoassay method for the purpose of determining Hb A$_{lc}$ in a biological fluid. Such immunoassay methods include the more classical techniques such as immunodiffusion, immunoelectrophoresis, agglutination techniques, and complement fixation, as well as more current techniques involving the use of specifically detectable labels such as radioimmunoassay and nonradioisotopic methods. The latter techniques can be practiced in a wide variety of formats such as the competitive binding format in which a labeled reagent is made to compete with the glucosylated analyte for binding to the antibody reagent. The amount of labeled reagent bound to the antibody reagent, or the free-species, consisting of the labeled reagent which is not so bound, is measured appropriately and can be functionally related to the amount of glucosylated analyte in the sample.

In radioimmunoassays, the free-species and boundspecies must be physically distinguished or separated in order to measure the label since the signal generated by the label is qualitatively the same in both species. Such a technique is known in the art as heterogeneous because of the phase separation requirement. Other heterogeneous immunoassay techniques are known including enzyme-labeled immunoassays, sometimes referred to as ELISA techniques (see U.S. Pat. No. 3,654,090), and fluorescent immunoassays (see U.S Pat. Nos. 4,201,763; 4,133,639 and 3,992,631).

Fairly recently, numerous immunoassay techniques have been developed which obviate the separation step through the use of a label whose detectable signal is modulated upon binding of the labeled reagent by a binding partner, e.g., antibody. Such techniques have become known as homogeneous and are preferred for use in the present invention because separations are not required and radioisotopes are not involved. Some such techniques are fluorescence quenching and enhancement (see U.S. Pat. No. 4,160,016), energy transfer immunoassay (see U.S. Pat. No. 3,996,345), and double antibody steric hindrance immunoassay (see U.S. Pat. Nos. 3,935,074 and 3,998,943). Particularly preferred homogeneous immunoassay techniques are those employing a label which is a participant in an enzyme-catalyzed reaction. Examples are the substrate-labeled immunoassay (see U.S. Pat. No. 4,279,992 and U.K. Patent Spec. 1,552,607), the prosthetic group (FAD)-labeled immunoassay (see U.S. Pat. No. 4,238,565), the enzyme modulator-labeled immunoassay, e.g., using inhibitor labels (see U.S. Pat Nos. 4,134,972 and 4,273,866), and enzyme-labeled immunoassay (see U.S. Pat. No. 3,817,837).

The monoclonal antibodies of the present invention are specific for binding to the glucosylated N-terminal peptide residue found in Hb A$_{lc}$. The antibodies are able to bind to the epitope in the native Hb A$_{lc}$ molecule when the N-terminal epitope is appropriately exposed. Steric access to the epitope can be obtained in any effective manner. Exposure of the epitope in the intact protein is understood to be accomplished by a physical or chemical denaturation or digestion at least in the region of the epitope. Such denaturation or digestion can be localized to the region of the epitope or can involve a more general, or even substantially complete denaturation of the tertiary, and additionally the secondary, structure of the protein, or partial or complete digestion of the protein.

Denaturation can be accomplished in a variety of ways including conventional treatment of the protein by physical means such as heat, sonication, high or low pH and, as is preferable, chemical denaturation by interaction with a chaotropic agent or chaotrope in solution. Useful chaotropic agents include, without limitation, guanidine, urea, and various detergents such as sodium dodecylsulfate (SDS) and others, without limitation, including deoxycholate and certain bile salts, 3-(3-cholamidopropyl)-dimethyl-ammonio- 1-propanesulfonate, organic solvents such as methanol, propanol, acetonitrile and certain salts such as potassium thiocyanate. Non-ionic detergents such as Triton X-100, nonidet NP-40 and octyl-glucosides can also function as protein denaturants. Inclusion of reagents (e.g., mercaptoethanol or dithiothreitol) that reduce disulfide bonds can be effective promoters of the denaturation process. Protein denaturation can be most effectively accomplished if combinations of chemical and/or chemical and physical means are used (e.g., guanidine and heat, guanidine and SDS, or guanidine and dithiothreitol). Particularly strong chaotropes such as guanidine are most preferred. Of course, denaturing conditions which result in substantial insolubilization, aggregation, or precipitation of the protein such that an insignificant amount of the exposed epitope is accessible to the solution for antibody binding will be avoided. A sufficient amount of the denatured protein must remain in solution or suspension in order to obtain useful immunobinding. The extent of solubilization necessary will depend upon the circumstances of the intended or desired binding.

A significant amount of Hb A$_{lc}$ in a particular blood sample can be denatured to expose the glucosylated epitope for antibody binding by combining the sample, e.g., whole blood or red cell hemolysate, with an aqueous solution of the chaotrope present at sufficient concentration to denature any Hb $A_{Ic}$ in the resulting aqueous mixture. Where whole blood is the sample, the chaotrope also serves to lyse red blood cells to release Hb and to inactivate proteases. In the case of guanidine, the concentration in the mixture will be preferably be greater than about 1.0 molar, with about 3 molar concentration being particularly useful. The denaturation process is significantly accelerated by heating the mixture for a short period of time. It has been found that at temperatures below 37° C., denaturation by the chaotrope can take from one to several hours, whereas at temperatures above 50° C. sufficient denaturation can be attained in a minute or less. In order to prevent significant denaturation of the antibody and other proteinaceous reagents to be subsequently added to the mixture, the sample-chaotrope mixture will normally be diluted as a separate step or by addition of reagent solutions to a level that the chaotrope is substantially ineffective to denature such reagents, yet will preserve the exposure of the epitope by preventing significant renaturation of the Hb $A_{Ic}$. For guanidine, this preferably requires dilution to a concentration less than about 1.0 molar, with about 0.3 molar being particularly preferred.

Non-limiting examples of proteolytic enzymes for use in the present invention for digestion including trypsin, chymotrypsin, proline-specific endoprotease, pepsin the proteolytic enzymes, as are known, are added to the assay mixture sufficient to prevent digestion of proteinaceous assay agents.

The invention will be further described in the following illustrative examples wherein all parts are by weight unless otherwise expressed.

EXAMPLE 1:

(a) An 11-amino acid peptide comprising the 8 N-terminal units of beta-hemoglobin plus two units of tyrosine plus a unit of cysteine was synthesized according to Gutte, B. and R.B. Merrifield; J. Am. Chem. Soc., 91:2, 501(1969), giving the following peptide:

$NH_2$-valine-histidine-leucine-threonine-proline-glutamic acid-glutamic acid-lysine-tyrosine tyrosine-cysteine-COOH.

To glucosylate this peptide, 200 mg of this purified peptide is reacted with 0.25 molar glucose in 20 ml of anhydrous pyridine for 48 hours at room temperature in the dark. The mixture is dried in vacuum. The resulting syrup is resuspended in 20 millimolar potassium phosphate, pH 2.95, and purified by HPLC.

The glucopeptide-bearing fractions are dissolved in 0.1 M triethylammonium acetate pH 8.5 and chromatographed over Affigel-601 boronate affinity resin (Biorad), whereby the glucopeptide is selectively adsorbed. The resin is washed with 0.1 M triethylammonium acetate pH 8.5 and the glucopeptide eluted with 0.1 M triethylammonium acetate pH 5.0. The eluate is lyophilized.

The product is resuspended in 1 ml of water, reacted with a 500 fold molar excess dithiothreitol (to restore the SH group of the cysteine) and the reduced peptide repurified by HPLC, and lyophilized. This glucopeptide is stored at $-20°$ C. under $N_2$ until further use.

(b) A KLH-MBS conjugate, as previously described, Lerner, R. et al, Proc. Natl. Acad. Sci. 78:3403(1981) is reacted with the product of (a) in a 2-fold molar ratio of glucopeptide to maleimide on the carrier, in 50 m molar potassium phosphate, pH 7.2, for 1 hour at room temperature.

(c) The solution in (b) is mixed with equal volumes of Freund's complete adjuvant to form a water-in-oil emulsion and 200 ug of conjugate is injected into BALB/cBy mice. The mice are boosted at 30 and 60 days, sacrificed, and their spleens used for fusion according to Kohler and Milstein, Nature 256:495(1975), producing numerous hybridomas. The hybridomas are screened to identify those which produced monoclonal antibodies specific for the glucosylated peptide epitope.

The screening for $A_{Ic}$ specific monoclonal antibodies is conducted using an ELISA format, where the antigen is absorbed onto polystyrene microtiter plates (Linbro) The antigens are purified human $A_{Ic}$ and non-glycosylated Ao hemoglobin. The $A_{Ic}$ is purified from a red blood cell hemolysate using two different chromatographic procedures. The first purification consists of binding glycosylated hemoglobin onto a boronate affinity resin as described by Pierce Chemical Co., Rockford, Ill., U.S.A., product no. 42,000. Typically 1 to 5 grams of hemoglobin are applied to 100 ml boronate resin, and the bound (glycohemoglobin) fraction elutes as described by Pierce Chemical Co., GlycoTest bulletin, product no. 42,000. The eluted glycohemoglobin fraction is equilibrated in low ionic strength buffer and chromatographed on an ion-exchange resin as described by McDonald, M. et al, J. Biol. Chem., 253: 2327–2332 (1978). The $A_{Ic}$ "peak" is analyzed by isoelectric focusing and by carbohydrate analysis using the thiobarbituric acid assay and the results confirm that this purification produced ultrapure $A_{Ic}$ hemoglobin in that the purified material has both carbohydrate and differed from normal Ao hemoglobin in isoelectric point. Similarly, Ao hemoglobin as purified by its property of not binding to the boronate affinity resin and chromatographing by ion-exchange as the Ao "peak" on the ion-exchange chromatographic purification. The pure $A_{Ic}$ and Ao hemoglobins are adsorbed onto separate microtiter plates (2 ug per 100 microliters PBS per well) overnight at 4° C. The plates are blocked in 1% BSA in PBS for 60 minutes at room temperature then washed 4 times in PBS. Supernatant from each hybridoma cell line is added to the $A_{Ic}$ and Ao plate and incubated at room temperature for 60 minutes. The plates are washed 4 times in PBS and a secondary antibody (rabbit-anti-mouse IgG-peroxidase, Miles Laboratories, Elkhart, Ind., U.S.A. at a 1:5000 dilution in 1% BSA in PBS) is applied and is subject to incubation for 60 minutes at room temperature. The plate is washed 4 times in PBS and 200 microliters of a substrate solution added (24.3 mM citric acid, 51.4M sodium phosphate, pH 5.3 containing 2.2 mM M o phenylenediamine and 5.2 mM hydrogen peroxide). The reaction is terminated after 20 minutes by adding 50 microliters of 8 M $H_2SO_4$ and the product of the peroxidase reaction is read at 492 mM.

From 200 starting hybridomas producing antibodies against hemoglobin, nine (9) are identified as being specific for the $A_{lc}$ epitope, whereas 191 reacts both with $A_{lc}$ and non-glucosylated hemoglobin. Since pre-immunized mouse serum has no detectable antibody response to Ao or $A_{lc}$ human hemoglobin by the ELISA procedure, the major immune response is against the eight peptide sequence that is shared in common with $A_{lc}$ and Ao. Since the synthetic peptide immunogen consists of eight amino acid residues, of the hemoglobin sequence, the major mouse immune response is directed against the peptide, and not the carbohydrate (191 of the 200 hybridomas reacting both with Ao and $A_{lc}$). As expected, the immunized mouse serum also has broadly cross reacting antibodies reactive both with Ao and $A_{lc}$ suggesting that no specificity for $A_{lc}$ is obtained unless hybridomas are screened for reactivity against $A_{lc}$ and not against Ao hemoglobin. The preferred hybridomas producing antibodies against $A_{lc}$ hemoglobin and not against Ao hemoglobin, were deposited with ATCC on Oct. 11, 1984, identified as ATCC HB 8639 and ATCC HB 8869, deposited on July 10, 1985.

(d) Identification of the peptides that compete with $A_{lc}$ for binding to antibody:

The following peptides are generated by enzyme digestion of the glucosylated 11-amino acid parent peptide:

Glyco-Val-His-Leu-Thr-Pro-Glu-Glu-Lys-Tyr-Tyr-Cys. (GLYCOPEPTIDE 1)

All peptide fragments are purified by HPLC and quantitated by amino acid analysis. Tryptic digestion of the parent peptide produced Glyco-Val-His-Leu-Thr-Pro-Glu-Glu-Lys. (GLYCOPEPTIDE 2)

A proline specific endoprotease produces

Glyco-Val-His-Leu-Thr-Pro. (GLYCOPEPTIDE 3)

The peptide Glyco-Val-His-FAD (GLYCOPEPTIDE 4) wherein the dipeptide is coupled to $N^6$-aminohexyl FAD and then glucosylated is made by the method of Carrico and Johnson, U.S. Pat. No. 4,255,566 and provided by Dr. Kin Yip and Dr. R. Buckler, Ames Division, Miles Laboratories, Elkhart, Ind., U.S.A.

Figure 2:
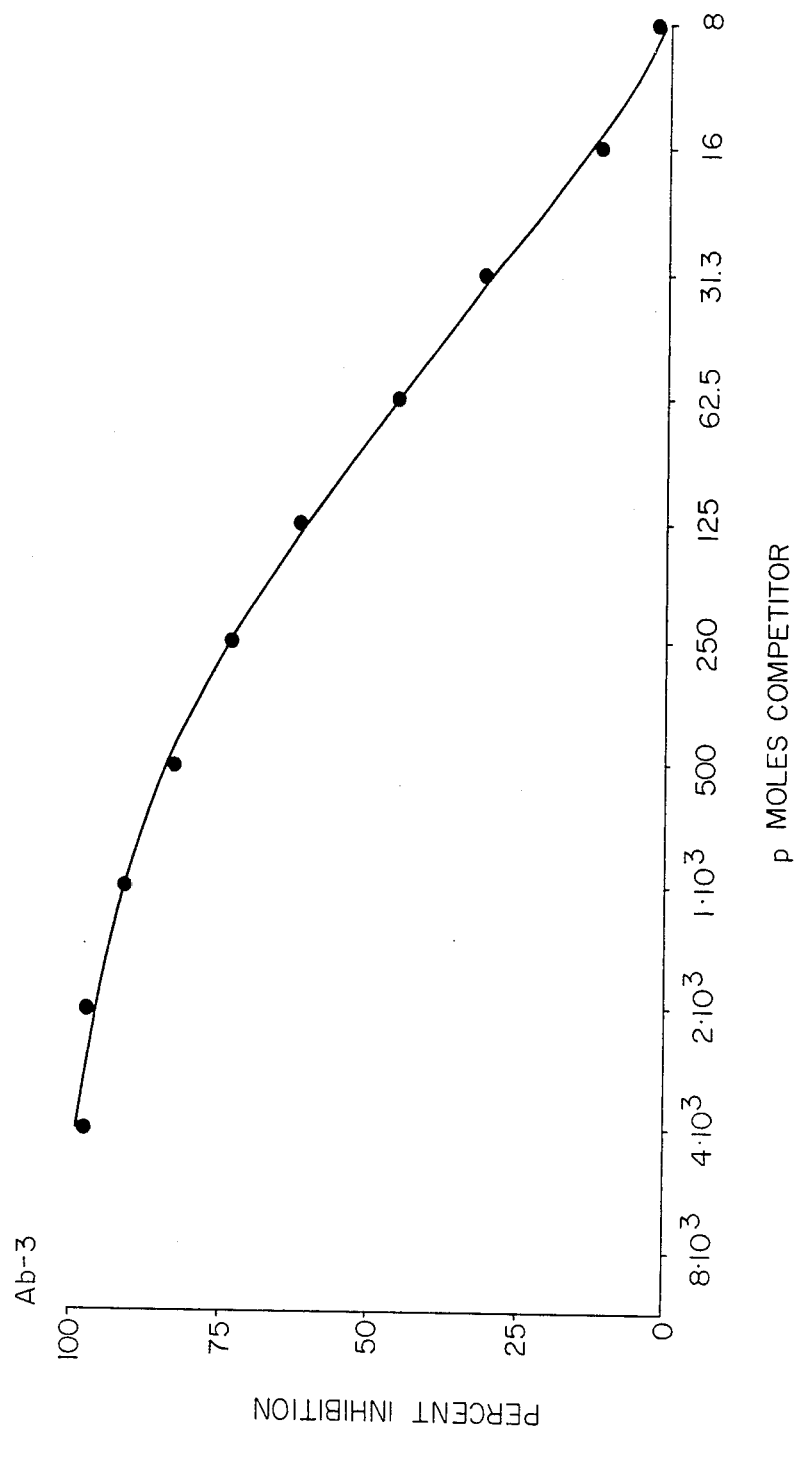
FIG. 2 is a plot depicting the inhibition of Ab-3 binding to $A_{Ic}$ by glycopeptide 3 (PEPTIDE 3). The competitive experiment was done as described in FIG. 1.
Figure 3:
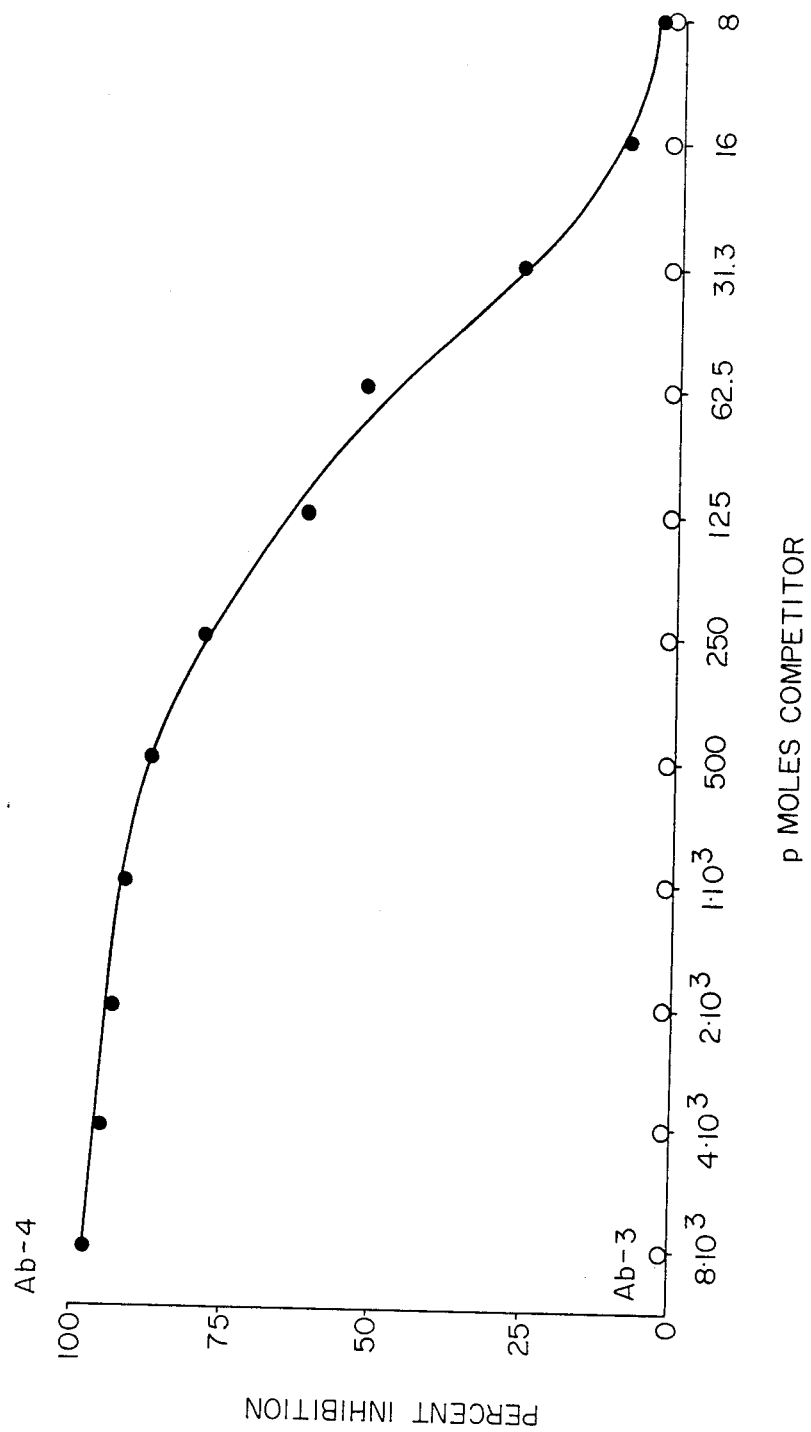
FIG. 3 is a plot depicting the inhibition of Ab-3 and Ab-4 by glycopeptide 4 (PEPTIDE 4) for $A_{Ic}$ binding.

In a typical competition assay, each peptide 8 n to 8 p moles in 100 $\mu$l PBS-7.2 mM $Na_2HPO_4$, 2.8 mM $NaH_2PO_4$, 127 mM NaCl, pH 7.4 is incubated with 100 $\mu$l monoclonal cell culture supernatant for 60 minutes at room temperature. This mixture is added to a polystyrene microtiter plate coated with 1 $\mu$g $A_{lc}$ hemoglobin/well. If the peptide competes with the antibody, the antibody is not free to bind to the immobilized $A_{lc}$. The plate is washed four times with PBS. A second antibody (rabbit anti mouse IgG coupled with horseradish peroxidase) is added for 30 minutes and the plate is washed in PBS. The substrate (o-phenylenediamine 2.2 mM), and hydrogen peroxide (0.012%) are added and the colored produced measured at 492 nm. The quantitation of the product reflects the extent of competition, e.g., no product indicates that the competing peptide totally blocked the antibody from binding to the immobilized $A_{lc}$. The results indicate that all four of the previously described glycopeptides including Glyco-Val-His-FAD are effective competitors. One of the antibodies, Ab-4, is totally blocked from binding to $A_{lc}$ by GLYCOPEPTIDES 1 to 4 (see FIGS. 1-3). Another antibody, Ab-3, is blocked by GLYCOPEPTIDES 1 to 3, but not by GLYCOPEPTIDE 4 (see FIGS. 1-3).

Peptides lacking the carbohydrate show no competition inhibition suggesting that the carbohydrate is an essential component of the epitope and provides the specificity for the antibodies' recognition of $A_{lc}$ hemoglobin (see FIG. 1).

EXAMPLE 2

Optimal Exposure of the $A_{1c}$ Epitope

Optimal reactivity of the human $A_{lc}$ epitope is seen following treatment of the native hemoglobin (in whole blood or hemolysate) with procedures or reagents which expose the epitope to the antibody combining site. The optimal exposure of the epitope can be accomplished by a physical denaturation (heat, sonication, etc.), by a chemical procedure involving classical denaturants (urea, guanidine, SDS, protease) or by a combination of physical and chemical procedures. Most effective is a procedure in which whole blood (50 microliters) is added to a 1 ml solution of 3M guanidine hydrochloride, 10 mM Tris-HCl, pH 7.4 and heated to 56° C. for greater than one minute. The resulting sample works optimally in subsequent immunoassays for the $A_{lc}$ epitope. The solution can be diluted ten fold in buffer, effectively diluting the guanidine to 0.3M, a concentration that has little if any effect on normal antibody-antigen interactions and enzyme activities, providing a suitable media for subsequent immunoassays.

EXAMPLE 3:

(a) 1 mg of the monoclonal antibody of Example 1(c) in 0.1 molar sodium borate buffer, pH 8.5 can be mixed with a 200-fold molar excess of fluorescein isothiocyanate (FITC) and reacted for 30 minutes at room temperature. The fluorescein labeled monoclonal antibody can be purified by gel filtration.

(b) A strip (polystyrene, cellulose, etc.) carrying COOH groups is dipped into 0.5 ml of unknown denatured hemolysate, pH 7.5. The strip is rinsed with buffer at pH 7.5 and immersed into the fluorescent monoclonal antibody of (a) in buffered solution, for 5 minutes at room temperature. The strip is again rinsed and the degree of fluorescence of the strip indicates the degree of $A_{lc}$ Hb in the unknown sample.

EXAMPLE 4

Coupling Monoclonal Antibody to Reagent Strip and its use in an immunoassay

Whatman #1 filter paper (7 cm) is placed in 20 ml ice-cold d-$H_2O$ and the pH of the solution is adjusted to between 10.5 -11.5 with 5M NaOH. Solution is monitored continuously throughout the activation and the pH is maintained between 10.5 -11.5 with dropwise addition of 5M NaOH. A small stir bar is placed in the bottom of the beaker containing the filter paper. The beaker is then placed in an ice filled petri dish which is placed on a magnetic stirrer. 1 gram of solid CnBr is added to the beaker and this is incubated with stirring for 20 minutes (on ice). Filter paper was removed from the solution and washed in 100 ml ice-cold distilled water (d-$H_2O$). It is then washed in ice-cold 0.2M $Na_2H PO_4$-citric acid buffer, pH 6.8. Antibody (1 mg/ml in 0.2M $Na_2HPO_4$-citric acid buffer (pH 6.8) is added and the coupling of antibody is allowed to proceed for 1 hour. Ethanolamine (10 ml of a 1 mM solution) is added to block unreacted sites (15 minutes) and the paper washed with phosphate buffered saline (PBS, 10 mM $NaH_2PO_4$, 140 mM NaCl, pH 7.5) to remove unreacted components.

This reagent strip is dipped into a standardized quantity of unknown denatured hemolysate containing a labeled competitor of the antibody binding for $A_{Ic}$ hemoglobin. A convenient competitor is the glycopeptide (GLYCOPEPTIDE no. 1) covalently coupled to horseradish peroxidase (HAPTEN-HRP). The strip is removed and rinsed with PBS. The amount of hemoglobin bound to the strip is measured (the quantity is inversely proportional to the $A_{Ic}$ in the sample and the $A_{Ic}$ hemoglobin can be quantitated by comparison to standard samples.

EXAMPLE 5

Enzyme Linked Immunosorbent Assay for $A_{Ic}$

A fixed volume of denatured blood hemolysate (100 $\mu l$) is added to polystyrene microtiter plates and allowed to bind at room temperature for 60 minutes. The plate is washed four times in PBS containing 0.05% Tween-20 (PBST). The monoclonal antibody (coupled to horseradish peroxidase) is added (100 $\mu l$, 1 $\mu g/ml$) in PBST and reacted for 30 minutes at room temperature. The excess antibody is removed with 4 washes of PBST. The substrate (o-phenylenediamine, 2.2 mM) and $H_2O_2$ (0.012%) in PBS are added and the reaction product measured at 492 nm. The color intensity reflects the quantity of $A_{Ic}$ present in the hemolysate when compared to standard values.

EXAMPLE 6

Radioimmunoassay for $A_{Ic}$

One hundred microliters of denatured blood hemolysate (220 n moles hemoglobin) is mixed with 7 n moles iodinated Glyco-Val-His-Leu-Thr-Pro-Glu-Glu-Lys-Tyr-Tyr-Cys (500,000 cpm/7 n moles). A monoclonal antibody is added in a quantity sufficient to bind to 50% of the glycosylated peptide if the blood hemolysate contains the normal (approximately 3%) $A_{Ic}$ hemoglobin. Higher hemoglobin $A_{Ic}$ values compete for the peptide thereby reducing the total number of counts bound by the antibody. The antibody can be recovered by immunoprecipitating with a second antibody (rabbit anti mouse IgG) or by adsorption onto protein A coated particles. The iodinated peptide bound to the antibody can be quantitated in a gamma isotope counter and reflects the quantity of $A_{Ic}$ present in the blood hemolysate when compared to standards.

EXAMPLE 7

Competitive Immunoassay Using Polystyrene Beads

This competitive immunoassay is based on the use of a fixed amount of hapten-label (as described in Example 9) that competes with $A_{Ic}$ in lysed whole blood for binding to the immobilized antibody. Since the antibody recognizes both the $A_{Ic}$ and hapten, the level of $A_{Ic}$ in the specimen determines the amount of hapten-label that binds to the antibody. Since the antibody is immobilized, all non-bound reactants can be removed by a simple washing step. The bound label can then be measured and compared to a standard for guantitation of $A_{Ic}$ in the original blood samples.

The assay is developed using whole blood as the specimen and can be divided into the steps listed below:

(1) Lysis of cells-denaturation of hemoglobin

Since the final assay requires less than 0.3 microliters of whole blood, an accurately pipettable volume of blood (5-50 $\mu l$ from a finger stick or from whole blood) is diluted into a denaturing solution (3M guanidine HCl, 10 mM Tris-HCl ph 7.5) and heated to 56° C. for 2 to 15 minutes Lower temperatures also work, but additional time is required for the complete denaturation of the sample. The denaturation (a) inactivates the clotting mechanisms if samples are not prepared in anticoagulants; (b) lyses the red cells; (c) denatures proteases, enzymes etc., and optimally exposes the $A_{1c}$ epitope on hemoglobin; (d) appears to either sterilize or inhibit the growth of microorganisms in the denatured blood sample even if the sample is non-aseptically prepared and handled (e.g., blood from a finger stick) and (e) results in a stable clinical sample that can be stored for days at room temperature without effect on the final assay.

(2) Dilution and Competition

An aliquot of the denatured whole blood is pipetted into a 10 fold volume of buffer containing the hapten-label. This effectively dilutes the hemoglobin to the proper concentration for the assay and dilutes the denaturant to a low concentration so as not to perturb the antibody or enzyme activity. The antibody coated bead is then added for a specified amount of time during which the antibody binds either the $A_{1c}$ hemoglobin or the hapten-HRP.

(3) Wash and Read

Following the competitive incubation, the bead is washed and the label read following the addition of an appropriate substrate. The signal is then compared to a standard and the amount of $A_{1c}$ present in the original whole blood sample determined.

The details of the assays used are summarized below:

Bead Coating Procedure

Polystyrene beads (¼ inch diameter with specular finish) are obtained from Precision Ball Company, Chicago, Ill., U.S.A. Lots are screened for beads that provided the lowest variability in multiple immunoassay determinations of the same sample. Prior to coating, beads are washed with absolute methanol followed by water. The methanol washed seemed to significantly lower the correlation of variation for multiple determinations of the same sample. An antibody solution (5 μg antibody/100 μl in 0.2M sodium borate, pH 8.5, 0.02% sodium azide) is then added to the damp beads and the beads rotated overnight at 4° C. The beads are then washed, blocked with 1% BSA in PBS containing 0.02% sodium azide. Typically, 500 to 1000 beads are coated at one time and used for a period of weeks with no evidence of loss of antibody activity. Coating experiments with radioactive antibody indicate that 0.5 ug of antibody binds per bead.

The beads are used in this immunoassay only because of their property of binding relatively high amounts of protein. The hydrophobic absorption of protein onto polystyrene is convenient, but certainly could be replaced by one of several procedures where proteins are covalently attached to polystyrene, functionalized resins, or silica. The polystyrene can also be in the form of a tube or cuvette.

The working protocol is summarized as follows:

(a) Dilute 50 microliters whole blood into 1.0 ml denaturing solution (3M guanidine-HCl, 10 mM Tris pH 7.5), heat to 56° C., 15 minutes, dilute again 100 μl into 1.0 ml denaturant.

(b) Add 50 microliters of the above solution to 0.5 ml phosphate buffered saline (PBS) pH 7.5 containing hapten-HRP. The incubations, washings and enzymatic reactions are conveniently conducted in 48-well polystyrene tissue culture plates.

(c) Add antibody coated bead and incubate 30 minutes at ambient temperature with rocking.

(d) Wash beads with buffer (PBS) (usually 3-1 ml changes).

(e) Add o-phenylenediamine substrate and hydrogen peroxide.

(f) Stop the reaction and read the product after 20 minutes. The above assay is used in establishing the clinical data described below. The standard curve is shown is FIG. 4. Competition using GLUCOPEPTIDE 1 is shown in FIG. 5. Evelation of normal and diabetic donors is shown in FIG. 6. The boronate affinity determination are performed exactly as described by Pierce Chemical Co. (GlycoTest, product no. 42,000).

EXAMPLE 8

Comparison of Antibody Specificity - Sheep Polyconal vs. Mouse Monoclonal Response A sheep is immunized, 4 sites, IM in Freund's complete adjuvant with the glycopeptide -KLH conjugate (4mg) of example 1(b). Boost injections are done similarly after 30 days and 60 days. The 60 day boost is in Freund's incomplete adjuvant. Preimmune serum, and immune serum is titered for its $A_{1c}$ and Ao specificity in an ELISA assay as described in Example 1(c). The results, (see FIG. 7) show that the synthetic glycopeptide stimulates an immune response against human hemoglobin, but that the immunoglobulins are not specific for $A_{1c}$ hemoglobin. In contrast, mouse monoclonal antibodies for $A_{1c}$ are quite specific for $A_{1c}$ when measured in the same assay (the ELISA assay of Example 1c—see FIG. 8). Attempts to immunoaffinity purify antibody specific for $A_{1c}$ from the sheep antiserum were not successful.

EXAMPLE 9

Preparation of Hapten-Label Conjugates

A conjuage of the GLYCOPEPTIDE 1 (HRP) was prepared. The hapten-HRP conjugate was prepared by reacting 15 mg horseradish peroxidase (HRP) with a 10 x molar excess of MBS (see Example 1b) in 50 mM sodium phosphate, 1 mM EDTA, pH 7.0. The MBS-HRP conjugate was purified by gel filtration (using the above buffer) and 0.34 mg of the glycopeptide hapten (PEPTIDE 1) was added. The final hapten-HRP conjugate was purified by gel filtration on HPLC and was used at a dilution of 1:1000–1:100,000 in the competitive immunoassay of Example 7.

It will be understood that the specification and examples are illustrative, but not limitative of the present invention and that other embodiments within the spirit and scope of the invention will suggest themselves to those skilled in the art.

What is claimed:

1. A monoclonal antibody or a fragment thereof comprising an antibody combining site, which binds specifically to the glucosylated form of the N-terminal peptide sequence in the beta-subunit of human hemoglobin.

2. A monoclonal antibody or a fragment thereof of claim 1 which binds specifically to a glucosylated peptide residue of the formula:

wherein Glyco-(NH)Val represents a nonenzymatically glucosylated valine residue and AA is a bond or one or more additional amino acid residues.

3. A monoclonal antibody or a fragment thereof of claim 2, wherein AA is a sequence of from 1 to 12 amino acids corresponding to the N-terminus of the beta-subunit of human hemoglobin.

4. A monoclonal antibody or a fragment thereof of claim 1 which is secreted by a murine hybridoma.

5. A monoclonal antibody or a fragment of claim 1 which has been raised against an immunogen comprising a glucosylated peptide chemically linked to an immunogenic carrier material, the glucosylated peptide having at least 2 amino acid units corresponding to the N-terminus of the beta-subunit of hemoglobin.

6. A monoclonal antibody or a fragment thereof of claim 5, wherein the immunogen is of the formula:

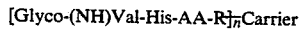

wherein Glyco-(NH)Val represents a nonenzymatic glucosylated valine residue, AA is a bond or one or more additional amino acid residues, R is a linking group, Carrier is an immunogenic carrier material, and n is on average from 1 to the number of available coupling sites on Carrier.

7. A monoclonal antibody or a fragment thereof of claim 6, wherein AA is selected from the group consisting of -Leu-, -Leu-Thr-, -Leu-Thr-Pro-, -Leu-Thr-Pro-Glu-, -Leu-Thr-Pro-Glu-Glu-, -Leu-Thr-Pro-Glu-Glu-Lys- and -Leu-Thr-Pro-Glu-Glu-Lys-Tyr-Tyr-Cys(SH), where -Cys(SH)-represents cysteine linked through its thiol group.

8. A monoclonal antibody or a fragment thereof of claim 6 wherein Carrier is an immunogenic protein or peptide other than human hemoglobin.

9. A murine monoclonal antibody or a fragment thereof of claim 1, which is secreted by hybridoma ATCC HB 8639.

10. A murine monoclonal antibody or a fragment thereof of claim 1, which is secreted by hybridoma ATCC HB 8869.

11. A monoclonal antibody or a fragment thereof of claim 1, which binds specifically to said glucosylated N-terminal peptide sequence in the beta-subunit of human hemoglobin $A_{1c}$ upon being exposed sufficiently to provide steric access thereto.

12. A monoclonal antibody or a fragment thereof of claim 11, wherein said glucosylated peptide sequence is exposed to the antibody binding site by physical or chemical denaturation or digestion.

13. A monoclonal antibody or a fragment thereof of claim 11, wherein said glucosylated peptide sequence is exposed to the antibody binding site by denaturation with a chaotropic agent.

14. A monoclonal antibody or a fragment thereof of claim 13, wherein the chaotropic agent is selected from the group consisting of guanidine, sodium dodecylsulfate, potassium thiocyanate and urea.

15. A monoclonal antibody or a fragment thereof of claim 11 which is of murine origin.

16. A monoclonal antibody or a fragment thereof claim 12 which is of murine origin.

17. A monoclonal antibody or a fragment thereof of claim 1, which binds specifically to said glucosylated N-terminal peptide sequence in the beta-submit of human hemoglobin $A1_c$ which has been adsorbed to a solid surface.

18. A monoclonal antibody or a fragment thereof of claim 17, wherein the solid surface is made of a carboxy-carrying material.

19. A monoclonal antibody or a fragment thereof of claim 17, wherein the solid surface is made of polystyrene.

20. A monoclonal antibody or a fragment thereof of claim 17, wherein the solid surface is made of cellulose.

* * * * *

UNITED STATES PATENT AND TRADEMARK OFFICE
CERTIFICATE OF CORRECTION

PATENT NO. : 4,727,036

DATED : February 23, 1988

INVENTOR(S) : William J. Knowles, et al.

It is certified that error appears in the above-identified patent and that said Letters Patent is hereby corrected as shown below:

| | |
|---|---|
| Abstract, line 14 | Correct --glucosylated-- |
| Col. 11, line 31 | After "pepsin" insert --and papain. In performing an immunoassay, inhibitors for-- |
| Col. 12, line 22 | After "(Linbro)" insert -- . -- |
| Col. 13, line 55 | After " 8 n" insert --moles-- |
| Col. 16, line 17 | Delete "guantitation" and substitute --quantitation-- |
| Col. 20, line 15 | Delete "-submit" and substitute -- -subunit-- |

Signed and Sealed this

Thirteenth Day of September, 1988

Attest:

DONALD J. QUIGG

Attesting Officer

Commissioner of Patents and Trademarks